United States Patent [19]
Levin

[11] Patent Number: 5,984,949
[45] Date of Patent: Nov. 16, 1999

[54] TISSUE HOOKS AND TOOLS FOR APPLYING SAME

[76] Inventor: John M. Levin, 412 Fairview Rd., Narberth, Pa. 19072

[21] Appl. No.: 08/944,920

[22] Filed: Oct. 6, 1997

[51] Int. Cl.[6] ........................................... A61B 7/04
[52] U.S. Cl. ............................. 606/216; 606/219
[58] Field of Search ................... 606/213–216, 606/219, 221

[56] References Cited

U.S. PATENT DOCUMENTS

| | | |
|---|---|---|
| 380,093 | 3/1888 | Cruice et al. . |
| 408,080 | 7/1889 | Carroll . |
| 2,669,747 | 2/1954 | Detaranto .............................. 606/216 |
| 2,817,339 | 12/1957 | Sullivan .................................. 606/221 |
| 3,385,299 | 5/1968 | Roy . |
| 4,428,376 | 1/1984 | Mericle . |
| 4,535,772 | 8/1985 | Sheehan . |
| 4,539,990 | 9/1985 | Stivala ................................... 606/216 |
| 4,602,634 | 7/1986 | Barkley . |
| 4,929,240 | 5/1990 | Kirsch et al. . |
| 4,950,284 | 8/1990 | Green et al. . |
| 5,026,390 | 6/1991 | Brown ................................... 606/221 |
| 5,047,047 | 9/1991 | Yoon ...................................... 606/216 |
| 5,158,566 | 10/1992 | Pianetti ................................. 606/216 |
| 5,209,756 | 5/1993 | Seedhom et al. . |
| 5,263,973 | 11/1993 | Cook ..................................... 606/216 |
| 5,423,857 | 6/1995 | Rosenman et al. . |
| 5,531,760 | 7/1996 | Alwafaie .............................. 606/216 |

*Primary Examiner*—Gary Jackson
*Attorney, Agent, or Firm*—Caesar, Rivise, Bernstein, Cohen, & Pokotilow, Ltd.

[57] ABSTRACT

A unitary tissue hook for permanently joining tissue segments together includes a base section and at least one pair of spaced apart arms. A first end of each of the arms is joined to the base section and a second end of each of the arms is provided with a tip. The tips of at least one pair of arms face each other for receiving and holding the tissue segments together. In a preferred form of the invention, the base section includes two pairs of spaced apart arms, with the arms in each pair being spaced apart in a first direction from each other and with each pair of arms being spaced from the other pair in a second direction that is transverse to said first direction. The preferred embodiments of the invention are non-deformable.

25 Claims, 6 Drawing Sheets

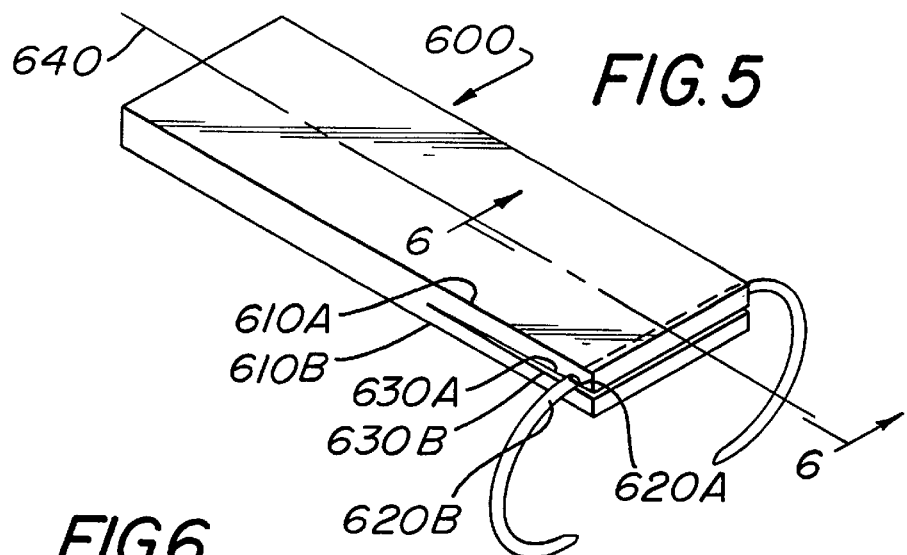
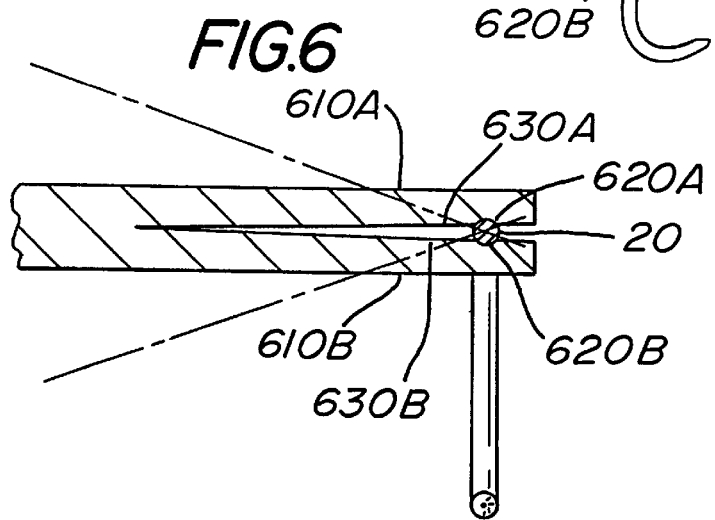
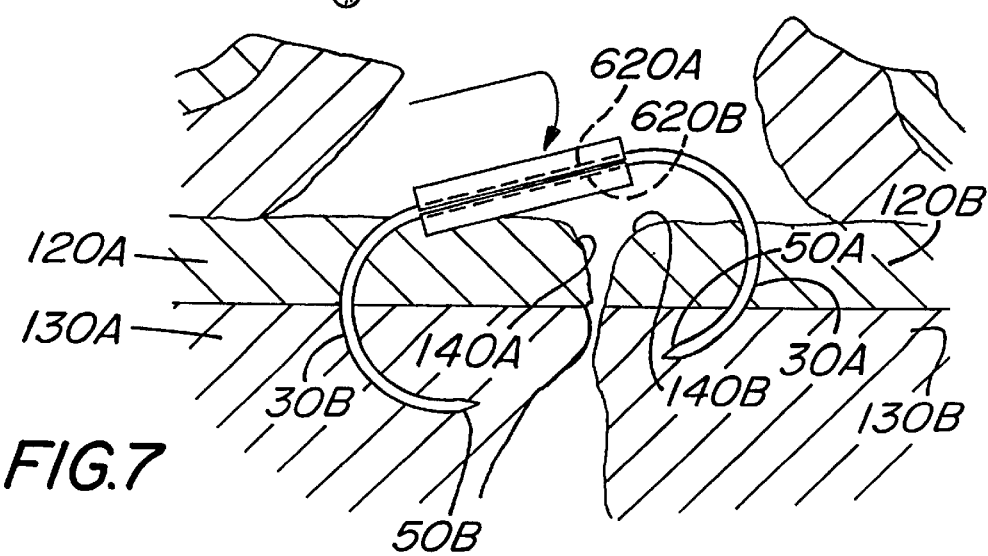

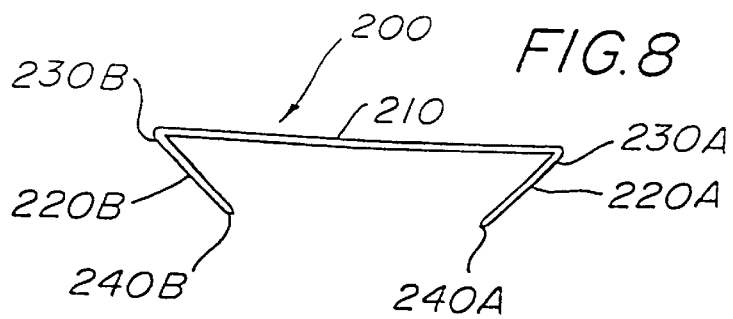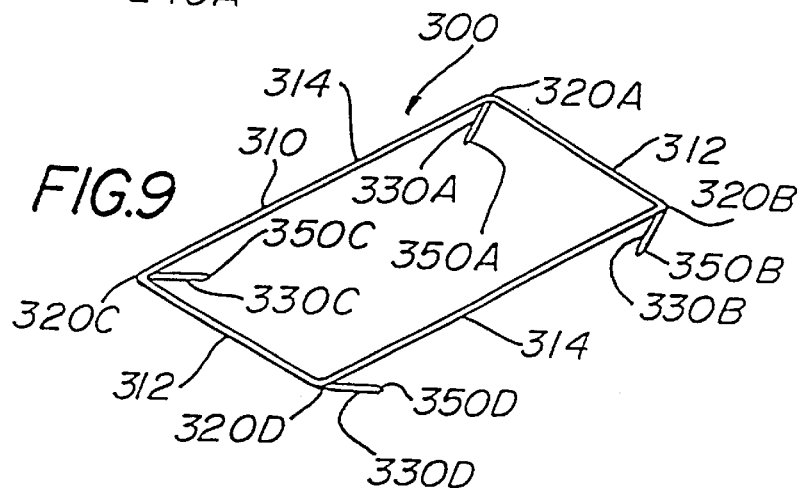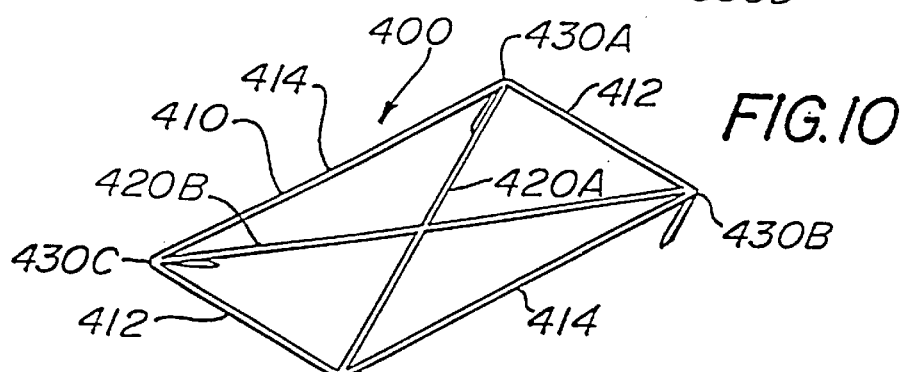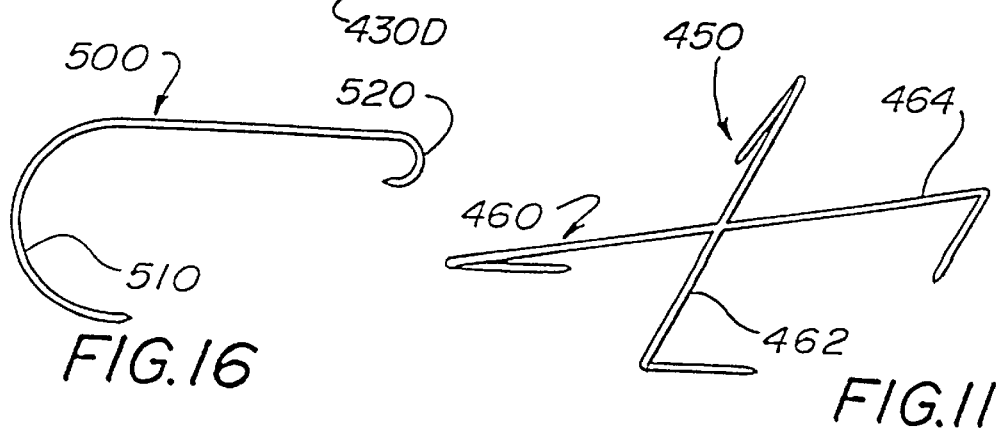

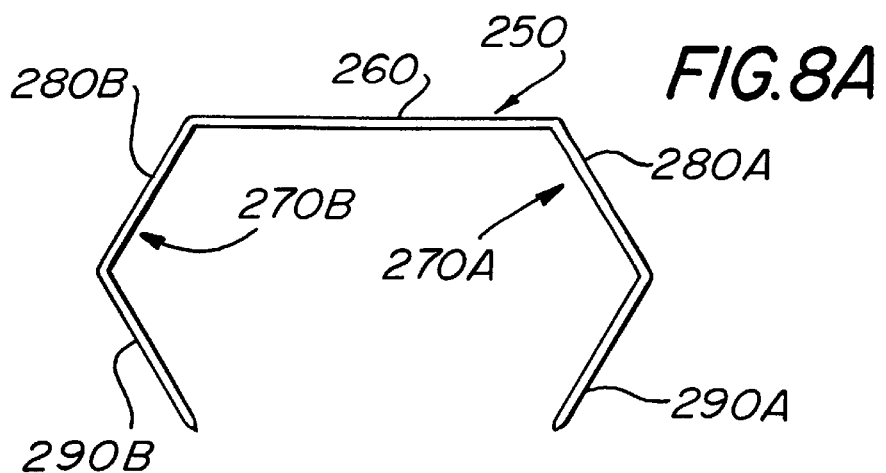
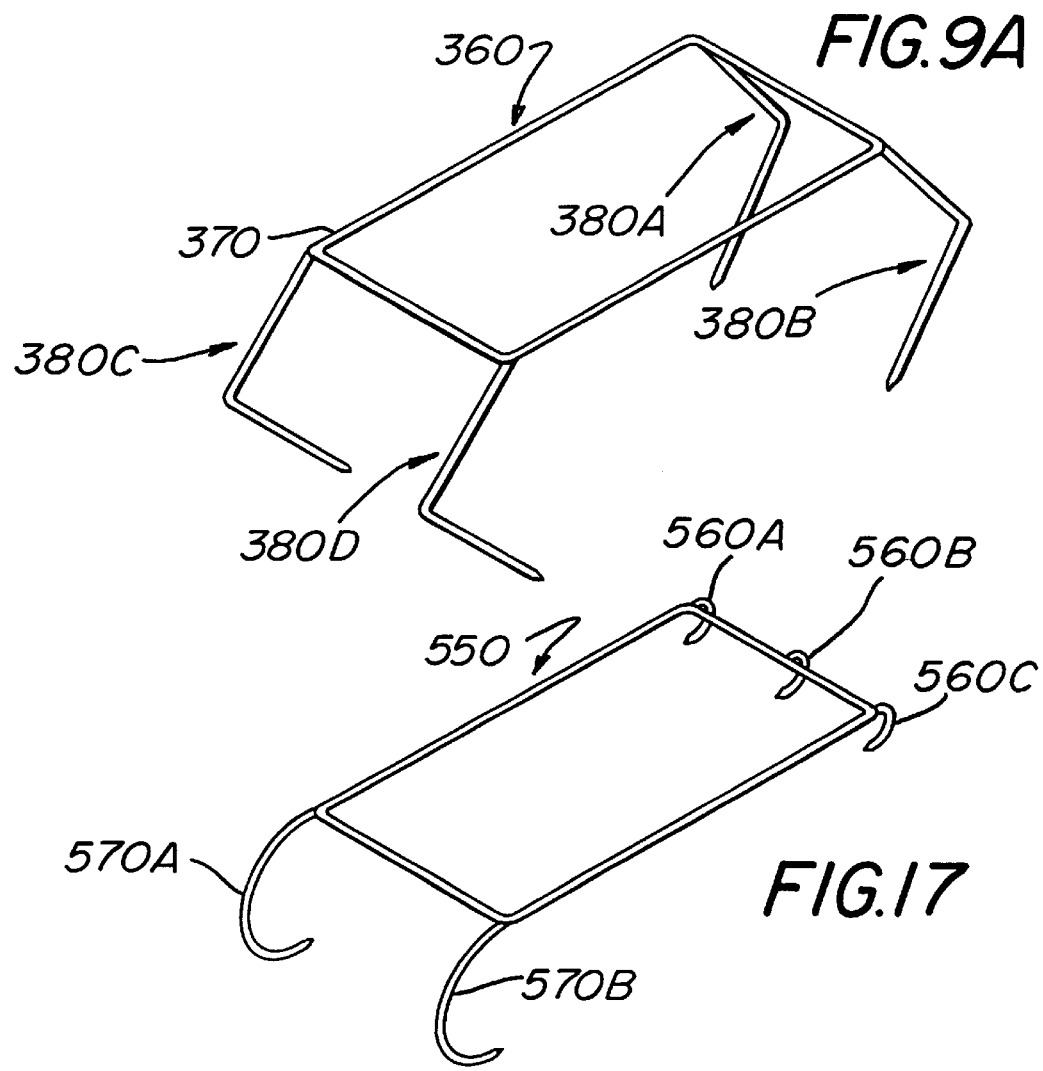

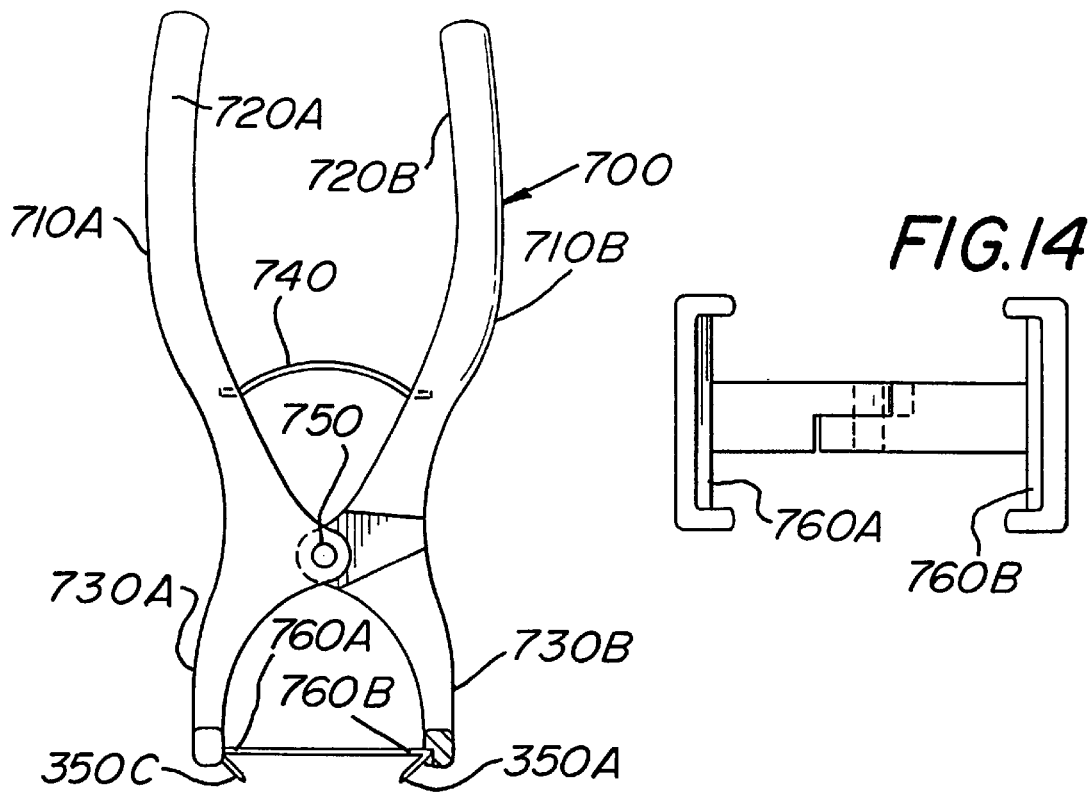
FIG. 14
FIG. 12
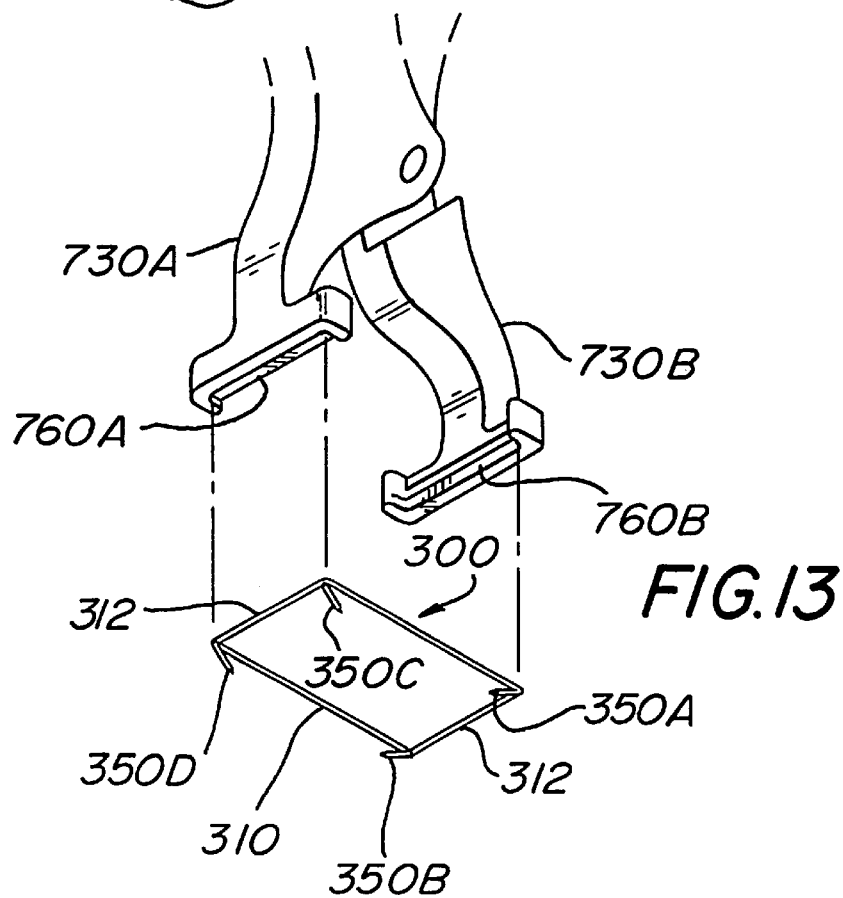
FIG. 13

TISSUE HOOKS AND TOOLS FOR APPLYING SAME

BACKGROUND OF THE INVENTION

This invention relates generally to surgical devices and more particularly to surgical devices for closing a wound, incision, or other defect in tissue, e.g., fascia, ligaments and tendons, and to tools for applying the same.

Various types of devices for closing incisions, wounds, and other defects in body parts (e.g., tissue) are known, such as surgical staples, clips and sutures. For example, U.S. Pat. No. 4,950,284 (Green et. al.) discloses a fascia clip of two pieces having an elongated base and a flexible strap that can be used to close an incision in fascial tissue.

U.S. Pat. No. 4,602,634 (Barkley) discloses a method and instrument for joining tissue with a staple and a receiver. The staple is placed on one side of two tissues to be joined and the receiver on the opposite side of the tissue. The legs of the staple are grasped and/or guided as they penetrate the tissue and are retained by the receiver. The legs of the staple are caused to penetrate body tissue and then be guided through and retained within the openings in the receiver.

U.S. Pat. No. 5,423,857 (Roseman et. al.) discloses a surgical staple having at least two legs that are pivotally mounted in a frame such that when the staple is inserted into tissue and the legs are rotated inwardly, the staple secures the tissue and the legs are locked in a fixed position.

U.S. Pat. No. 4,929,240 (Kirsch et. al.) discloses a surgical microclip particularly adapted for microvascular anastomoses having a pair of arcuate legs interconnected by a briding section. The clip is formed of a unitary piece of biologically acceptable, plastically deformable material, that further has two spaced "ears" to facilitate handling and removal of the clip. Also disclosed is a tool for applying the clip.

U.S. Pat. No. 5,209,756 (Seedhom et al.) discloses a fixation device for securing a prosthetic ligament to a bone. The device comprises a bone staple having a head portion by means of which the staple can be driven into the bone, and a pair of legs extending from the head and having ends engagable into the bone. The device also is provided with a stirrup for guiding the driving movement of the staple and arranged also to cooperate with the staple in order to enable the prosthetic ligament to engage the staple and the stirrup and to be securable to the bone upon completion of driving of the staple into the bone. This staple also can be used for securing tissues.

U.S. Pat. No. 4,428,376 (Mericle) discloses a one-piece, self-locking, molded plastic staple useful as a tissue fixation device in surgical procedures. The staple has opposed, pointed, L-shaped legs hinged to a horizontal bridging member having expanding cam surfaces on each end. The staple is closed by rotating the legs 90 degrees. Also disclosed is a series of staples joined by a common member. This latter arrangement permits a plurality of staples to be loaded into a repeating staple setting instrument, wherein each staple is severed from the common member during the application process.

A typical problem encountered with the use of prior art staples, clips and sutures is that they tend to be applied in a manner that imposes an excessive "squeezing" force on the joined body parts. When connecting tissue segments, this excessive force cuts off, or greatly reduces, blood flow to the area at which the tissue segments are being connected, thereby causing ischemia, which impairs the healing process.

Although many of the above discussed surgical staples, clips and sutures have been used with some success, there is a need for an improved attachment device that eliminates or greatly reduces ischemia, is inexpensive to manufacture, is easy and fast to use and results in less pain and discomfort to the patient.

OBJECTS OF THE INVENTION

Accordingly, it is a general object of this invention to provide improved hooks for closing incisions, wounds and other defects in tissue, (e.g., fascia, ligaments and tendons) wherein the hooks have numerous advantages over prior art connecting devices, such as sutures and staples, as follows:

1. The hooks of this invention are easier and less expensive to manufacture than prior art sutures and staples.
2. The hooks of this invention are easier to apply than prior art sutures and staples.
3. The hooks of this invention are faster to apply than prior art sutures and staples.
4. The hooks of this invention are less expensive for hospitals to purchase than prior art sutures and staples.
5. The hooks of this invention provide decreased pain to the patient relative to sutures and staples because the tissue is neither crushed excessively, as occurs with fascial staples, nor completely encircled, as occurs with sutures (all surgical tissues swell post-operatively; surgery being a form of controlled injury).
6. The hooks of this invention provide decreased ischemia because there is no excessive crushing of tissue, as with fascial staples, or complete encircling of body tissues as with sutures; therefore, providing better healing and less complications, as well as less pain for the patient.
7. The hooks of this invention provide a superior device for closing fascial tissue defects caused by laproscopic trocar punctures. Prior to this invention there was no ideal or very effective technique for accomplishing this function.
8. The hooks of this invention require less skill and effort to apply than prior art sutures and staples.
9. The hooks of this invention eliminate suture granuloma.
10. The hooks of this invention are easier to re-adjust after initial placement than prior art sutures and staples.

It is a further object of this invention to provide specialty tools for use in attaching hooks to tissue, wherein such tool can be separated easily from the hook after the hook has been so attached.

SUMMARY OF THE INVENTION

These and other objects of certain preferred embodiments of this invention are achieved by providing a unitary non-deformable hook for closing incisions, wounds, and other defects in body tissue (e.g., fascia, ligaments and tendons). The hooks of this invention comprise at least one pair of arms, wherein one end of each arm is joined to a base section and the other end of each arm terminates at a tip, with the tips of each pair of arms facing each other. The tips are slightly rounded (e.g., like that of an atraumatic surgical needle), but sufficiently pointed to pierce the tissue. If desired, the tips may be provided with a barb in order to hook together and retain the tissue without back slippage.

Reference through this application to the tips of each pair of arms "facing each other" is not limited to a construction in which the tips of each pair of arms are directly opposite each other, but includes constructions wherein the tip on one side of the base section is transversely offset from the respective tip on the other side of the base section.

Reference throughout this application to certain preferred embodiments of the hooks of this invention being "non-deformable" means that they have substantially the same configuration before use and after they are in their final position for engaging and retaining body tissue segments to be joined together. Within the definition of "non-deformable" hooks are hooks that are so rigid that they do not deform at all in use, and hooks that are minimally deformable in use, i.e., have some "minimal give" in use, but when deformed, have an elastic memory for their initial non-deformed configuration (that is, their configuration before use). In the non-deformable hooks of this invention, the spacing between the tips of each pair of arms and the position of the arms relative to the base section remain substantially the same before use of the hook and after the hook engages and retains the tissue segments in their desired position. That is, internal forces (or pressure) imposed upon the hooks of this invention by the tissue being acted upon by such hooks, including any increase in intra-abdominal pressure, will not significantly deform or alter the initial configuration of the hooks of this invention; the only deformation or alteration that possibly occurs being the result of minimal give existing in such hooks.

Because of the aforementioned "non-deformable" characteristic of certain preferred embodiments of the hooks of this invention, said hooks, in use, are not compressed or otherwise deformed by an external force applying means or device, either to cause the arms of the hook to be moved toward each other or to move toward the base of the hook.

The foregoing "non-deformable" characteristic or property of certain preferred embodiments of the invention does not preclude a slight expansion, or enlargement, of the spacing between the tips of each pair of arms resulting from an outward force imposed on the arms of the hook by the engaged tissue segments. However, as noted earlier, any such expansion of the spacing between the tips of each pair of arms only will be minimal, with the arms having an elastic memory for their initial configuration. Such characteristic of these hooks will allow for the arms to resist the force imposed on them so as to preclude an expansion of the spacing between the tips of each pair of arms that is so great as to permit the tissue segments to be joined together to move apart and impair the healing process.

In the most preferred embodiments of the present invention, the non-deformable hooks of this invention are so stiff that the configuration of the hooks before and after they are applied to the tissue is exactly the same. That is, in the most preferred embodiments, the configuration of the hooks when joining tissue segments together will not be altered in any way, either by internally imposed forces (e.g., from the tissue) or externally imposed forces (e.g., from a human or machine).

The "non-deformable" characteristic or property of certain preferred embodiments of the hooks of this invention distinguishes such hooks from prior art sutures, staples and clips that are deformed either by internally-imposed or externally-imposed forces, either during or after engagement with the tissue segments to be joined together. For example, sutures are deformed to conform to the shape of the tissue being enclosed, and staples are deformed into the shape that is dictated by the structure of the stapling device, as well as the thickness, density and contour of the tissue being stapled. Such deformation of prior art sutures, staples and clips preclude them from being within the definition of "non-deformable" because they do not retain substantially the same configuration both before and after engaging the tissue segments to be joined together.

The non-deformable hooks of this invention are easier and faster to apply than prior art sutures and staples, require less skill and effort to apply than prior art sutures and staples, and are easier to re-adjust after initial placement than prior art sutures and staples. Also, the non-deformable hooks of this invention provide decreased pain to the patient and decreased ischemia relative to sutures and staples because the tissue is neither excessively crushed, as occurs with fascial staples, nor completely encircled, as occurs with sutures; therefore, providing better healing and less complications.

In accordance with this invention, certain hooks are not required to be non-deformable, i.e., they may be deformable. As will be explained in detail hereinafter, these latter hooks differ from prior art deformable staples in the relative configuration of the spaced apart arms and/or the number of arms.

In one preferred use, one or more hooks is (are) applied to tissue segments (e.g., fascial tissue) to be joined by piercing and hooking a first tissue segment with one tip of a pair of arms, pulling the tissue segments into engagement with each other and then piercing and hooking a second tissue segment with the second tip of the same pair of arms, with the edges of the tissue segments to be joined abutting each other. In the preferred uses, this joining process is carried out with the non-deformable hooks of this invention, without deforming the hooks, which often excessively crimps the tissue.

Hook applicators for applying the hooks also form a part of this invention. These applicators include specially configured jaws to grip the base section of the hook during the hook-application function, and then to easily release the hook after the hook has been applied to the tissue segments to be joined.

DESCRIPTION OF THE DRAWINGS

Other objects and many of the intended advantages of this invention will be readily appreciated as the same becomes better understood by reference to the following detailed description, when considered in connection with the accompanying drawings wherein:

FIG. 5 is an enlarged isometric view of an applicator of the present invention holding a hook to be applied to opposed tissue segments to be joined together;

FIG. 6 is an enlarged cross-sectional view taken along line 6—6 of FIG. 5;

FIG. 7 is a sectional view through tissue being joined together, illustrating the manner in which the applicator of FIG. 5 is employed;

FIG. 8 is a side elevational view of another embodiment of a hook in accordance with the present invention;

FIG. 8A is a side elevational view of yet another embodiment of a hook in accordance with the present invention having multiple arm segments;

FIG. 9 is an isometric view of yet another embodiment of a hook in accordance with the present invention having an open rectangular base section;

FIG. 9A is an isometric view of yet another embodiment of a hook in accordance with the present invention having an open rectangular base section and multiple arm segments;

FIG. 10 is an isometric view of yet another embodiment of a hook in accordance with the present invention having a combined rectangular and X-shaped base section;

FIG. 11 is an isometric view of yet another embodiment of a hook in accordance with the present invention having an X-shaped base section;

FIG. 12 is a front elevational view of another hook applicator in accordance with the present invention;

FIG. 13 is an enlarged fragmentary isometric view of a portion of the applicator shown in FIG. 12;

FIG. 14 is a bottom view of the applicator shown in FIG. 12;

FIG. 16 is a side elevational view of another embodiment of a hook in accordance with the present invention having a pair of arms of different radius; and FIG. 17 is an isometric view of yet another embodiment of a hook in accordance with the present invention having multiple arms of a different radius.

DETAILED DESCRIPTION OF THE PREFERRED EMBODIMENTS

Figure 15:
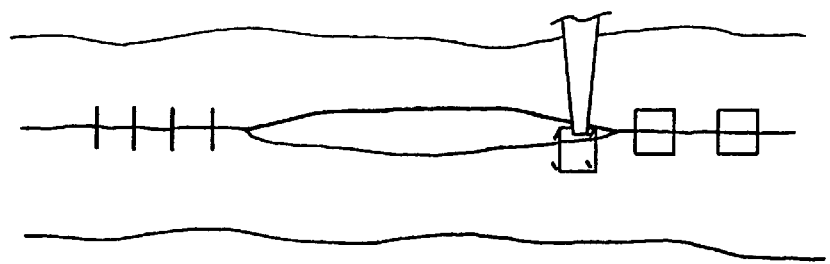
FIG. 15 is a plan view illustrating the manner in which hooks in accordance with the present invention can be employed to join the edges of tissue segments.

Referring now in greater detail to the various figures of the drawing wherein like reference characters refer to like parts, there is shown at 10 in FIGS. 1, 2, 4A and 4B, one embodiment of a non-deformable tissue hook in accordance with this invention. Shown in FIG. 9 is the preferred embodiment of a non-deformable tissue hook in accordance with this invention, which will be described later. In accordance with broader aspects of this invention, this latter embodiment also can be deformable. Shown in FIGS. 3, 8 and 8A are other embodiments of a non-deformable tissue hook in accordance with this invention, which will be described later. Shown in FIGS. 9A, 10, 11, 16 and 17 are still other embodiments of a tissue hook in accordance with this invention that can be either deformable or non-deformable and will be described later. Shown in FIGS. 5–7 and 12–14 are tools for application of the tissue hooks of this invention, which tools will be described later. Shown in FIG. 15 are various embodiments of tissue hooks of this invention joining tissue segments (e.g., fascia, ligaments and tendons) together.

Figure 1:
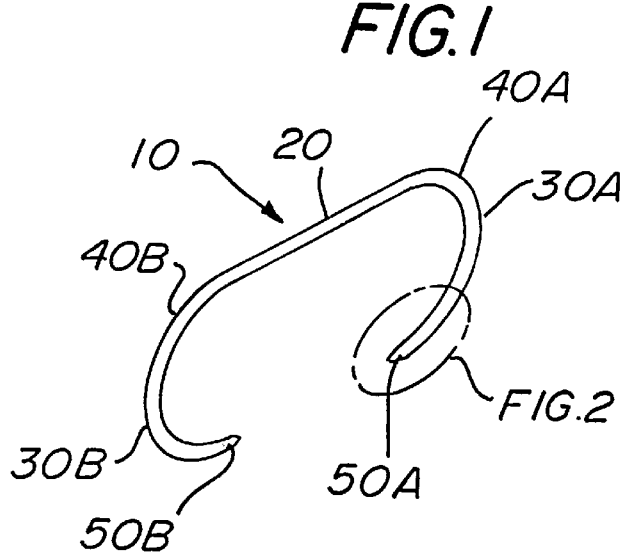
FIG. 1 is an isometric view of one embodiment of a hook in accordance with the present invention.

Referring to FIG. 1, the hook 10 is a unitary member of a generally C-shaped configuration comprising a substantially linear base section 20 and a pair of arms 30A and 30B joined thereto. Each of the arms 30A and 30B is arcuate and has an end 40A and 40B, respectively, joined to the base section 20, and an opposed, distal end 50A and 50B, respectively, in the form of a tip. The tips 50A and 50B are spaced-apart from each other and face each other for receiving and holding tissue, e.g., fascia, ligaments and tendons, together.

Figure 2:
FIG. 2 is an enlarged fragmentary view of the arm and tip portion of the hook of FIG. 1.
Figure 3:
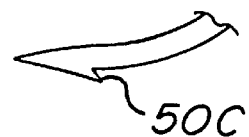
FIG. 3 is an enlarged fragmentary view of another embodiment of an arm and tip portion of a hook of the present invention, wherein the tip is provided with a barb.

As is shown in FIG. 2, the tips 50A, 50B of the arms 30A, 30B (only one tip being shown at 50A) are slightly rounded, most preferable as employed in an atraumatic surgical needle, but sufficiently pointed to pierce tissue segments to be joined together. Such a tip construction, while sufficiently pointed to easily and reliably pierce tissue segments to be joined, is not so pointed so as to injure the person applying the hook of this invention.

Shown in FIG. 3 is another embodiment of the tips (only one tip being shown) having a barb 50C for piercing and holding together tissue segments to be joined. This is an optional feature that can be employed, if desired, to prevent back slippage.

Figure 4B:
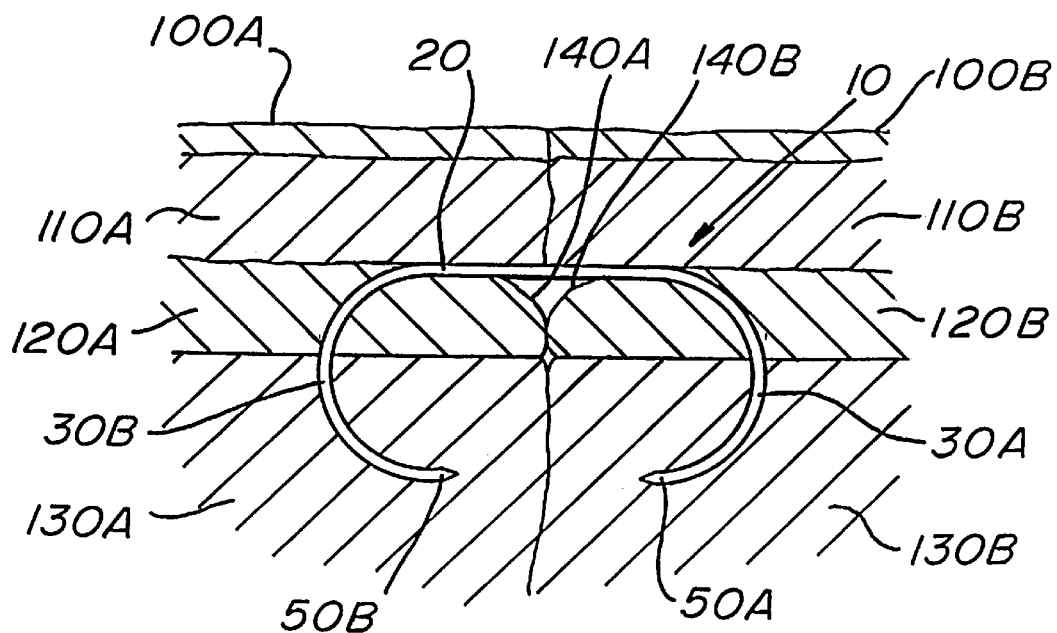
FIG. 4B is a sectional view similar to FIG. 4A, but showing the hook of FIG. 1 in its final position and configuration disposed within and joining the edges of opposed fascial tissue segments.
Figure 4A:
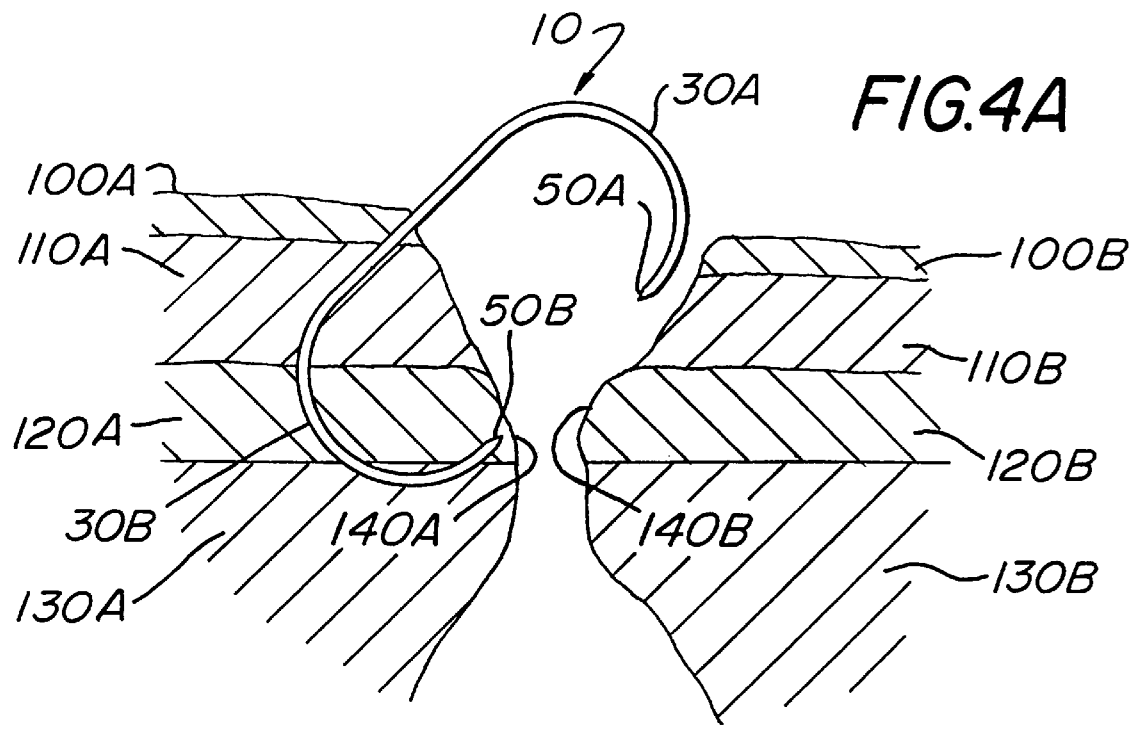
FIG. 4A is a sectional view through tissue being joined together showing the hook of FIG. 1 being inserted into one fascial tissue segment.

Shown in FIGS. 4A and 4B is the application of the hook 10 to the fascial tissue. The hook 10 is applied by first piercing and hooking one of the tips, e.g., the tip 50B, into the fascial tissue segment 120A. Thereafter, fascial tissue segments 120A, 120B to be connected together are pulled into engagement with each other with forceps or other desired gripping device, and the application of the hook 10 is completed by piercing and hooking the opposed tip 50A into the second fascial tissue segment 120B. Hook 10, as well as the other hooks of this invention, are easier and faster to apply and require less skill and effort to apply than prior art sutures and staples. Also, the hooks of this invention are easier to re-adjust after initial placement than prior art sutures and staples.

Referring to FIG. 4B, both the tips 50A and 50B pierce the fascial tissue segments 120A and 120B and muscle layers 130A and 130B. When the hook 10 receives and holds the tissue segments (fascial tissue segments 120A and 120B and muscle tissue layers 130A and 130B), it forms and retains a smooth abutment and alignment of edges 140A and 140B, as shown in FIG. 4B.

It should be understood that the hook 10 can be dimensioned so that the tips 50A and 50B pierce only the fascial tissue segments 120A and 120B, without extending into the muscle layers 130A and 130B. It also should be understood that the hook 10, as illustrated in FIG. 4B, is "non-deformable," i.e., it provides its tissue retaining function without being substantially deformed from its original configuration by either externally or internally (e.g., tissue) imposed forces. This is a very important feature of certain preferred embodiments of the present invention, including hook 10. The non-deformable hooks of this invention provide decreased pain to the patient and decreased ischemia relative to sutures and staples because the tissue being engaged is not crushed, as occurs with fascial staples, nor completely encircled, as occurs with sutures, thereby providing better healing and less complications than prior art staples and sutures.

Referring to FIG. 8, another embodiment of a unitary, non-deformable tissue hook is shown at 200. The hook 200, like the hook 10, comprises a base section 210 and a pair of arms 220A and 220B joined thereto. Each of the arms 220A and 220B is a linear member having one end thereof 230A and 230B, respectively, joined to the base section 210, and an opposed, distal end thereof 240A and 240B, respectively, in the form of a tip. The arms 220A and 220B form an acute angle with the base section 210. Like the tips 50A and 50B of hook 10, the tips 240A and 240B of hook 200 are spaced apart from each other and face each other for receiving and holding tissue segments together. It should be understood that the hook 200 can include arms of different shapes, e.g., arcuate and linear.

Referring to FIG. 8A, yet another embodiment of a tissue hook in accordance with this invention is illustrated at 250.

In the hook 250, the arms 270A and 270B form an angle with the base section 260. The arm 270A comprises a pair of linear segments 280A and 290A, and the arm 270B comprises a pair of linear segments 280B and 290B. It should be understood that the multiple segments 280A, 280B, 290A and 290B need not be linear as shown in FIG. 8A. For example, some or all of the multiple segments can be arcuate. It also should be understood that the number of segments that comprise each arm is not a limitation on the broadest aspects of this invention, nor do the number of segments in both arms of the hook have to be the same.

Referring now to FIG. 9, the preferred embodiment of a non-deformable tissue hook of this invention is shown at 300. The hook 300 comprises an open rectangular base section 310 having opposed short legs 312 and opposed long legs 314. Four arms 330A, 330B, 330C and 330D are located at the four corners, respectively, of the base section 310. The arms 330A and 330C form a first pair of arms and the arms 330B and 330D form a second pair of arms. The opposed, distal ends 350A and 350C of the fist pair of arms 330A and 330C, respectively, constitute tips. The tips 350A and 350C are spaced apart from each other in a first direction and face each other for receiving and holding tissue segments together. Similarly, the opposed, distal ends 350B and 350D of the second pair of arms 330B and 330D, respectively, constitute tips. The tips 350B and 350D also are spaced apart from each other in the same first direction as the tips 350A, 350C, and face each other for receiving and holding tissue segments together.

The first pair of arms 330A and 330C is spaced from the second pair of arms 330B and 330D in a second direction substantially perpendicular to the aforementioned first direction. It should be understood that depending on the configuration of the hook of this invention, the above mentioned first direction need only be transverse, and not substantially perpendicular, to the second direction. In the preferred embodiment, the first pair of arms 330A and 330C also defines a plane that is substantially parallel to a plane defined by the second pair arms 330B and 330D.

The hook 300 preferably is applied to tissue segments (e.g., fascia, ligaments and tendons) in a similar manner as the hook 10, as illustrated in FIGS. 4A and 4B, i.e., by piercing and hooking each tissue segment one at a time. By having two pairs of arms in the hook 300, the hook helps establish and maintain alignment of the edges of the joined tissue segments in directions both across and along the joining line of said tissue segments to be joined together, and also prevents linear slippage in a direction along the joining line.

Referring to FIG. 10, a hook that is similar in construction and application to hook 300 is illustrated at 400. Hook 400 differs from hook 300 by employing linear crossing segments 420A and 420B as part of the base section 410. Each of the linear segments 420A and 420B joins diametrically opposed corners 430A, 430B, 430C and 430D, respectively, of the outer rectangular frame of the base section 410. The outer rectangular frame is formed of opposed short legs 412 and opposed long legs 414 in the same manner as the base section 310 of the hook 300 (See FIG. 9).

Referring to FIG. 11, another embodiment of a hook in accordance with this invention is shown at 450. This hook is similar in construction and application to the hooks 300 and 400 illustrated in FIGS. 9 and 10, respectively. Hook 450 differs from hooks 300 and 400 by having a base section 460 in the form of an X-shaped member having crossing legs 462, 464 only.

It should be understood that each of the arms in the hooks shown in FIGS. 9, 10 and 11 need not be comprised of a single linear segment. Such arms can be arcuate and/or comprise multiple segments. For example, it may be desirable to have a hook 360, as is illustrated in FIG. 9A, that is similar in construction and application to hooks 250 and 300 of FIGS. 8A and 9, respectively. That is, hook 360 has an open rectangular base section 370, like that of the base in hook 300, and each arm 380A, 380B, 380C and 380D is formed from a pair of linear segments, like that of the arms 270A and 270B of FIG. 8A.

Certain preferred embodiments of non-deformable hooks of this invention can be formed from any suitable material having the required non-deformable property, e.g., metal (e.g., Titanium), plastic or resorbable material that is minimally deformable and is normally biased in the direction of the initial configuration (i.e., before application) of the hook in order to retain the hook in the same configuration both before and after its application to tissue segments to be joined together. In the most preferred construction, the non-deformable hooks of this invention may be made from a high carbon spring steel, such as the type employed in the manufacture of fish hooks, with the most preferred non-deformable embodiments of this invention having the same rigidity as a number 2 or number 4 fish hook.

Shown in FIG. 15 is the application of a series of hooks in accordance with various embodiments of this invention to an incision, wound, or other defect in the tissue. The number of hooks of this invention needed to close an incision, wound, or other defect in a tissue is not a limitation of the present invention, and is a function of the nature of the incision, wound, or defect. For some applications, such as in closing a laproscopic trocar fascial defect, it may be possible to employ only a single hook of this invention. In other applications, multiple hooks are required.

In an exemplary embodiment of this invention, the length of the hook is approximately 2.0 cm., the height of the hook (i.e., the linear distance from the tip to the base section) is approximately 1.0 cm. and the space between the tips is approximately 1.0 cm. However, the dimensions of the hook can be varied within wide limits, as is dictated by the anatomical structure of the patient.

It should be understood that in the preferred embodiments of this invention, the hooks are employed to join together fascial tissue segments. However, the particular type of tissue segments that are joined together do not constitute a limitation on the broadest aspects of this invention.

The hooks of this invention may by be employed in inguinal hernia repair by connecting the conjoined tendon to the thinner, shelving edge of the inguinal ligament (Poupart's ligament). For this application, the opposed arms of the hook most desirably are of different sizes and/or number (quantity), due to the fact that the conjoined tendon is thicker than the inguinal ligament. For example, as illustrated in FIG. 16, a C-shaped variant of a hook of this invention for use in inguinal hernia repair is shown at 500 and has one curved arm 510 on a radius of approximately 0.75 cm. for engaging the conjoined tendon and a second curved arm 520 on a radius of approximately 0.15 cm. for engaging the inguinal ligament.

The specific size/shape of the arms and base section do not constitute a limitation on the broadest aspects of this invention. Similarly, the number of arms on each side of the base section does not have to be the same. It is within the scope of the broadest aspects of this invention to include a different number of arms having a different size radius on each side of the base section of the hook. By way of illustration, it may be desirable for the hook described above for inguinal hernia repair to have more arms 560A, 560B and 560C (e.g., 3) having a radius of approximately 0.15 cm than arms 570A and 570B (e.g., 2) having a radius of approximately 0.75 cm, as is illustrated in FIG. 17.

It also should be understood that in all hook variants of this invention the tips preferably are slightly rounded, like an atraumatic surgical needle, and, if desired, provided with a barb, in the same manner as disclosed in connection with the hook 10.

Referring to FIGS. 5–7, a specialty tool for applying a hook of this invention that includes only a single pair of arms (e.g., hooks 10, 200, 250 and 500) is illustrated at 600. For ease of discussion, the tool 600 will be described for use in applying hook 10 shown in FIG. 1. However, it should be understood that use of the tool 600 for applying hook 10 is the same as the use of the tool for applying other preferred embodiments of the hooks of this invention having only a single pair of arms.

The tool 600 comprises two resilient spring loaded jaws 610A and 610B having inner surfaces 630A and 630B, respectively, that face each other. The jaws 610A and 610B are normally biased in a closing direction. The inner surfaces 630A and 630B have opposed recesses 620A and 620B, respectively, to receive the base section 20 of hook 10 during the hook applying operation, as is shown in FIGS. 5 and 6. As can be seen best in FIG. 5, the tool 600 has a longitudinal axis 640, and the recesses 620A and 620B extend in a direction that is transverse to said longitudinal axis.

The hook 10 is applied to the fascial tissue using the tool 600 in a manner similar to that which was described for FIGS. 4A and 4B. Specifically, after the recesses 620A and 620B of tool 600 receive the base 20 of hook 10 therein, the tool 600 is rotated about its longitudinal axis 640 so that the tip 50B pierces and hooks the fascial tissue segment 120A and, if desired, muscle tissue 130A. The fascial tissue segments 120A and 120B are then pulled towards each other so that edges 140A, 140B abut. The tool 600 is then rotated in the other direction so that the tip 50A pierces and hooks fascial tissue segment 120B and, if desired, muscle tissue 130B. The application of hook 10 using the tool 600 is completed by moving the tool 600 away from the joined fascial tissue segments 120A and 120B, which movement causes the spring loaded jaws 610A and 610B to easily and automatically release hook 10. This release action can be enhanced by providing a slightly angled exit ramp at the edge of recesses 620A, 620B closest to the free end of the jaws 610A, 610B.

Referring to FIGS. 12–14, a specialty tool for applying a hook of this invention that includes four extreme points in its base section (e.g., hooks 300, 360, 400, 450 and 550) is illustrated at 700. As described in this application, the hooks for use with the tool 700 include two pairs of arms, but that is not a limitation for using said tool.

For ease of discussion, the tool 700 will be described for use in applying the preferred hook 300 shown in FIG. 9 to tissue. However, it should be understood that use of the tool 700 for applying hook 300 is the same as the use of said tool for applying other hooks of this invention having four extreme points in the hook's base section.

The tool 700 is similar to the shape of pliers and includes two members 710A and 710B connected by a spring 740 and a pivot pin 750. Proximal sections 720A, 720B on one side of the pivot pin 750 constitute gripping and actuating arms of the tool 700, and distal sections 730A, 730B on the other side of the pivot pin constitute hook-engaging jaws of the tool. The spring 740 between the gripping and actuating arms 720A and 720B normally biases the jaws 730A and 730B in the closing direction. The distal, or forward, end of the jaws 730A and 730B have opposed recesses 760A and 760B, respectively, as is seen best in FIG. 14.

The recesses 760A and 760B receive the opposed short legs 312 of the rectangular base section 310 of hook 300, as shown in FIG. 13. When the rectangular base section 310 is engaged in the recesses 760A and 760B, the tips 350A, 350B, 350C and 350D of hook 300 extend beyond the distal end of the jaws 730A and 730B, as is shown in FIG. 12 (which shows only two of the tips 350A and 350C). This extension of the tips 350A, 350B, 350C and 350D beyond the distal end of the jaws 730A and 730B is necessary to expose said tips to piercing and hooking tissue segments together.

The hook 300 is applied to the tissue using the tool 700 in a manner similar to that which was described for applying hook 10 using the tool 600. The difference being that both tips 350C and 350D pierce and hook one tissue segment and both tips 350A and 350B pierce and hook a second tissue segment. Once the hook 300 engages the tissues to be joined together, the arms 720A and 720B of tool 700 are manually squeezed together against the opposing force of spring 740, which movement causes the jaws 730A and 730B to easily and automatically release hook 300.

Although the above mentioned tools 600, 700 are specially designed for use in the application of the hooks of this invention, the hooks of this invention can be applied by using conventional prior art tools, such as tools normally employed to hold and guide a suture needle during a suturing operation, e.g., a standard ratcheted surgical needle holder.

While the preferred hook embodiments of the present invention are "non-deformable," as defined above, the broader concepts of this invention include certain hooks that need not be non-deformable. These latter hooks are applied to tissue segments to be joined together in a manner similar to that of the non-deformable hooks of this invention. The difference being that once the deformable hooks engage the tissue segments, the arms of such hooks may be deformed by bending the arms to better grip the tissue segments and prevent the edges of the tissue segments from pulling apart.

The deformable hooks of this invention differ from prior art staples, which are also deformable to hold tissue segments together, in that the deformable hooks of this invention comprises any of the following: (1) a pair of arms with the tips of each arm facing each other and each arm having a different size radius (e.g., hook in FIG. 16); (2) multiple pairs of arms with the tips of the arms of each pair of arms facing each other (e.g., hooks in FIGS. 9, 9A, 10 and 11); or (3) the configuration of the arms as described in (1) or (2) but having a different number of arms on each side of the base section (e.g., hook in FIG. 17). The deformable hooks of this invention can have more than one of the foregoing properties/configurations.

The deformable hooks of this invention can be formed from any suitable metal (e.g., Titanium), plastic or resorbable material that is capable of being deformed into a final, tissue holding configuration by external force from a human and/or machine.

Without further elaboration, the foregoing will so fully illustrate my invention, that others may by applying current or future knowledge readily adapt the same for use under various conditions of service.

I claim:

1. A unitary non-deformable tissue hook for joining an edge of a tissue to an edge of a second tissue, said hook having a base section with opposed first and second ends; spaced apart arms having first ends joined respectively to said first and second ends of said base section; a tip at a second end of each of said arms, said tips being oriented for piercing said tissue; wherein the number of arms joined to said first end of the base section is different from the number of arms joined to said second end of said base section.

2. A unitary non-deformable tissue hook for joining an edge of a tissue to an edge of a second tissue, said hook comprising a base section having an X-shaped configurations; at least one pair of spaced apart arms, wherein a first end of each of said arms is joined to a respective end of said base section; a tip at a second end of each of said arms for piercing said tissue; wherein said tips of said at least one pair of arms being oriented for receiving and holding said tissue together.

3. The non-deformable tissue hook of claim 2 comprising multiple pairs of arms, wherein said arms of each of said pairs of arms are spaced apart from each other in a first direction, and each of said pair of arms is spaced from the other pairs of arms in a second direction transverse to said first direction.

4. The non-deformable tissue hook of claim 2 comprising multiple pairs of arms, wherein said arms of each said pairs of arms define a plane that is substantially parallel to the plane formed by the other of said pairs of arms.

5. A unitary non-deformable tissue hook for joining an edge of a tissue to an edge of a second tissue, said hook comprising a base section having an open rectangular configuration including elements joining diametrically opposed corners of said rectangular base section; at least one pair of spaced apart arms, wherein a first end of each of said arms is joined to a respective end of said base section; a tip at a second end of each of said arms for piercing said tissue; wherein said tips of said at least one pair of arms being oriented for receiving and holding said tissue together.

6. The non-deformable tissue hook of claim 5 comprising multiple pairs of arms, wherein said arms of each of said pairs of arms are spaced apart from each other in a first direction, and each of said pair of arms is spaced from the other pairs of arms in a second direction transverse to said first direction.

7. The non-deformable tissue hook of claim 5 comprising multiple pairs of arms, wherein said arms of each said pairs of arms define a plane that is substantially parallel to the plane formed by the other of said pairs of arms.

8. A unitary non-deformable tissue hook for joining an edge of a tissue to an edge of a second tissue, said hook comprising a base section; multiple pairs of arms, a first end of each arm being joined to the base section and a second end of each arm including a tip for piercing said tissue; wherein said arms of each of said pairs of arms are spaced apart from each other in a first direction, and each of said pairs of arms is spaced from the other pairs of arms in a second direction transverse to said first direction.

9. The non-deformable tissue hook of claim 8, wherein said first and second directions are substantially perpendicular to each other.

10. The non-deformable tissue hook of claim 8 comprising two pairs of arms.

11. A unitary non-deformable tissue hook for joining an edge of a tissue to an edge of a second tissue, said hook comprising a base section of an open rectangular configuration; multiple pairs of arms, each arm being joined at one end to said base section and having a tip at the other end for piercing said tissue; said arms of each of said pairs of arms being spaced apart from each other in the first direction, and each of said pairs of arms being spaced from the other pairs of arms in a second direction transverse to said first direction.

12. A tool for use in applying a tissue hook to tissue segments, said tissue hook including a base section, spaced apart arms joined at one end to said base section and a tip joined at a second end to each of said arms for piercing said tissue, said tool including moveable jaws having confronting recesses for receiving the base section of the hook therein, said moveable jaws being normally biased in a closing direction for retaining a base section of the hook in the recesses in the jaws during the step of applying a hook to the tissue segments to be joined together, said jaws being moveable in a direction opposed to said normally biased direction for releasing the base section of the hook from the jaws after the hook has been applied to the tissue segments.

13. The tool of claim 12, wherein said opposed jaws have inwardly facing surfaces with the recesses therein for receiving the base section of the hook.

14. A unitary tissue hook for joining an edge of a tissue to an edge of a second tissue, said hook comprising:
   (a) a base section;
   (b) at least one pair of spaced apart arms, wherein a first end of each of said arms is joined to a respective end of said base section;
   (c) a tip at a second end of each of said arms for piercing said tissue;
   (d) wherein said tips of said at least one pair of arms face each other for receiving and holding said tissue together;
   (e) wherein the number of arms joined to one end of the base section is different from the number of arms joined to the other end of said base section.

15. A unitary tissue hook for joining an edge of a tissue to an edge of a second tissue, said hook comprising:
   (a) a base section having a first side and a second side, wherein said first side is opposite to said second side;
   (b) multiple pairs of spaced apart arms, wherein a first end of each of said arms is joined to a respective end of said base section;
   (c) a tip at a second end of each of said arms for piercing said tissue;
   (d) wherein said tips of each of said pairs of arms face each other for receiving and holding said tissue together;
   (e) wherein said arms of each of said pairs of arms are spaced apart from each other in a first direction, and each of said pair of arms is spaced from the other pairs of arms in a second direction transverse to said first direction.

16. The tissue hook of claim 15, wherein said base section is of an open rectangular configuration.

17. The tissue hook of claim 15, wherein said first and second directions are substantially perpendicular to each other.

18. The tissue hook of claim 15, wherein said arms of each of said pairs of arms define a plane that is substantially parallel to the plane formed by the other of said pairs of arms.

19. The tissue hook of claim 15 comprising two pairs of arms.

20. The tissue hook of claim 18 comprising two pairs of arms.

21. The tissue hook of claim 15, wherein the shape of said arms of at least one of said pairs of arms is different from each other.

22. The tissue hook of claim 15, wherein the size of said arms of at least one of said pairs of arms is different from each other.

23. The tissue hook of claim 15, wherein the number of said arms on said first side of said base section is different from the number of said arms on said second side of said base section.

24. The tissue hook of claim 23, wherein the shape of said arms of said at least one of said pairs of arms is different from each other.

25. The tissue hook of claim 23, wherein the size of said arms of said at least one of said pairs of arms is different from each other.

* * * * *